United States Patent
Seip et al.

(12) 
(10) Patent No.: US 6,432,663 B1
(45) Date of Patent: Aug. 13, 2002

(54) MULTI-CHANNEL PLATE

(75) Inventors: William Francis Seip, Baltimore; Donald Ray Callihan, Cockeysville; Paul Ernest Goldenbaum, Hampstead., all of MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/517,270

(22) Filed: Mar. 2, 2000

(51) Int. Cl.[7] .............................. C12Q 1/02; C12Q 1/00; C12M 1/00; C12M 1/34
(52) U.S. Cl. ................... 435/29; 435/4; 435/283.1; 435/287.1; 435/305.1; 435/305.2
(58) Field of Search ..................... 435/29, 4, 283.1, 435/288.4, 287.1, 305.1, 305.2

(56) References Cited

U.S. PATENT DOCUMENTS 5,429,951 A * 7/1995 Bradwell ..................... 436/515

* cited by examiner

Primary Examiner—Louise N. Leary
(74) Attorney, Agent, or Firm—Bruce S. Weintraub, Esq.

(57) ABSTRACT

The present invention relates to a novel container and process, and more specifically, to a rectilinear plastic container whose interior is divided into two or more channels (a multi-channel plate) which is filled with a microbial growth medium and is utilized in a process for enumeration of microorganisms found in clinical or industrial samples. Different microbial growth media may be placed in adjacent channels of the rectilinear plastic container for the process of the present invention. The process of the present invention demonstrates a more efficient and rapid means to identify and enumerate microorganisms in a sample.

28 Claims, 2 Drawing Sheets

MULTI-CHANNEL PLATE

FIELD OF THE INVENTION

The present invention relates to a novel container and process, and more specifically, to a rectilinear plastic container whose interior is divided into two or more channels which is filled with a microbial growth medium and is utilized in a process for enumeration of microorganisms found in clinical or industrial samples. Different microbial growth media may be placed in adjacent channels of the rectilinear plastic container for the process of the present invention. The process of the present invention demonstrates a more efficient and rapid means to identify and enumerate microorganisms in a sample.

BACKGROUND OF THE INVENTION

Analysis of various specimen samples for the quantity of microorganisms they might contain is routinely done. Analysis is also performed to determine the identity of microorganisms in a sample. Samples can come from many sources and include clinical, i.e., urine, blood, pus, etc., and industrial (e.g. food, water, environmental or pharmaceutical) sources.

Enumeration and identification of the number of microorganisms, including yeasts, bacteria and fungi, in a sample is important for many reasons. This knowledge can assist a doctor in determining the level of and the type of infection in a patient and can therefore assist in determining appropriate treatment. Enumeration and identification of bacteria or other microbes from water and wastewater samples is routinely done to see if the water meets acceptable health standards. Likewise, food products such as meats and dairy products are also tested.

Methods of enumerating microorganisms are known, but suffer from significant drawbacks. In perhaps the most routinely used method, the sample suspected of containing microorganisms is serially diluted, typically in ten-fold dilutions but also in two-fold or five-fold dilutions. Making five or six serial ten-fold dilutions is typical. Each diluted sample is then spread onto a separate plated agar-based medium using a constant volume, for example 10, 50 or 100 uL of each dilution. To ensure accuracy, these samples are usually plated in duplicate or triplicate. The inoculated plates are then incubated. Incubation periods of 16–24 hours are standard. After the incubation period, the plates are examined for growth of microorganisms.

Typically, some plates in the dilution series will show little or no growth, while others will show growth of so many colonies that accurately counting them is not feasible. Typically, one or two plates at a specific dilution will yield a countable number of colonies. Generally, plates demonstrating between 30 and 300 colonies are considered countable and representative of the starting viable population. Knowing the dilution of the sample used on the counted plate, one can readily calculate the number of microorganisms in the original sample.

As the description of this process makes clear, this so-called colony enumeration method is both time consuming and, labor intensive and thus expensive. For each sample tested, many media-containing plates are prepared and used, while only a few yield results which provide useful information.

Thus, many plates are in effect wasted, significantly increasing the cost of conducting such a test. Moreover, waiting for the incubation of the microorganisms until there are visually observable colonies takes at least one working day. In some instances, for example where the public health is involved, such a waiting period can delay implementation of decisions needed to prevent further cases of diseases caused by the microorganism.

An alternative to this well accepted enumeration technique was suggested in *Biotechniques*, vol. 23, 648 (1997). The proposed alternative used a track-dilution technique whereby six 10-fold serial dilutions of a sample containing an unknown quantity of bacteria were plated onto a single square agar plate. 10 uL samples were spotted in a column on the agar surface along one side of the square using a micropipet in ascending order of bacterial concentration. The plate is tipped at an angle to allow the samples to run down the plate and then allowed to dry before incubation. This method used less materials and took less time since fewer plates were inoculated. The results achieved were not statistically different from the counts achieved with the separate plate method.

While this method is an improvement over the prior method, it still suffers from drawbacks. For example, the possibility that the different tracks of the dilution will cross over into each other exists when the plates are tilted. Further, this method requires the use of a single growth media in the plate. Additionally, the possibility of crossover makes such a system difficult to automate.

It is therefore an object of the present invention to have a device used to enumerate microorganisms where there is no possibility of crossover contamination between adjacent samples. It is also an object to have a device where identification and enumeration can be simultaneously performed.

It is also an object of this invention to permit greater flexibility in the testing and enumeration process by permitting the enumeration or identification of more than one microorganism in a sample.

Another object of the invention is to decrease the time to analyze and enumerate outgrowth of organisms in samples.

Another object of the invention is to determine susceptibility of microorganisms to antibiotics by establishing concentration gradients, in an appropriate gelled growth matrix, within each channel.

Another object of the invention is to allow portions of the same sample to be inoculated onto different media.

Automation of microbial enumeration is yet another object of the present invention.

SUMMARY OF THE INVENTION

The present invention is a square or rectangular plastic dish, also referred to as a rectilinear plastic container having a depth sufficient to contain a microbial growth medium in an amount that is adequate to support growth of microorganisms. The dish preferably has a lugged lid which can preserve the moisture level of the growth media as well as its sterility and the chemical integrity of the growth media. This dish is preferably separated by a predetermined number of spacers to create parallel channels or spaces which run the length of the dish. The troughs thus formed may be of uniform depth or may be formed so as to create a wedge-shaped profile.

Microbial enumeration is performed by placing a sample that is known or suspected of containing a microorganism, at a predetermined dilution, at the top of each channel. The dish is then tilted to allow the sample to flow along the length of the channel. Alternatively, a spreading device is used to distribute the sample from one end of a channel to the other. Appropriate incubation conditions are applied. After a sufficient amount of time has passed to permit microbial growth the channels are inspected either mechanically, by a high-resolution camera, for example, or visually. Based on the microorganism counts made at this time, the total number and concentration of microorganisms in the original sample can be calculated.

DETAILED DESCRIPTION OF THE INVENTION

Figure 1:
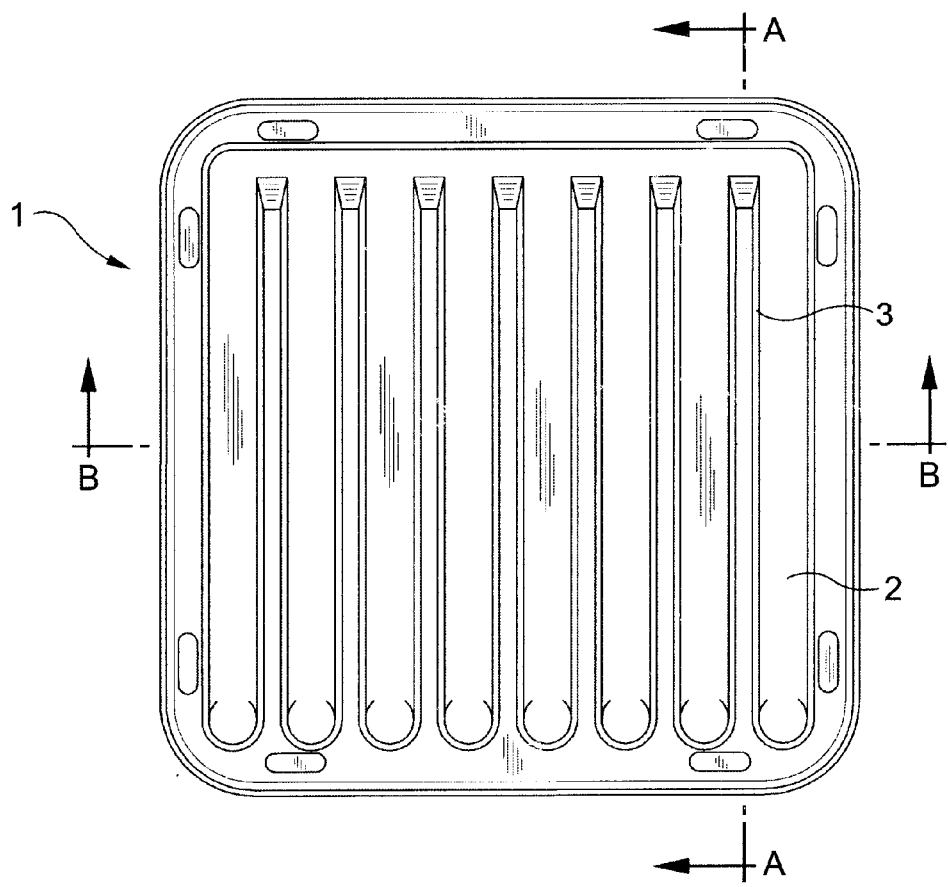
FIG. 1 is an overhead view of a multi-channel dish in accordance with the present invention.
Figure 2:
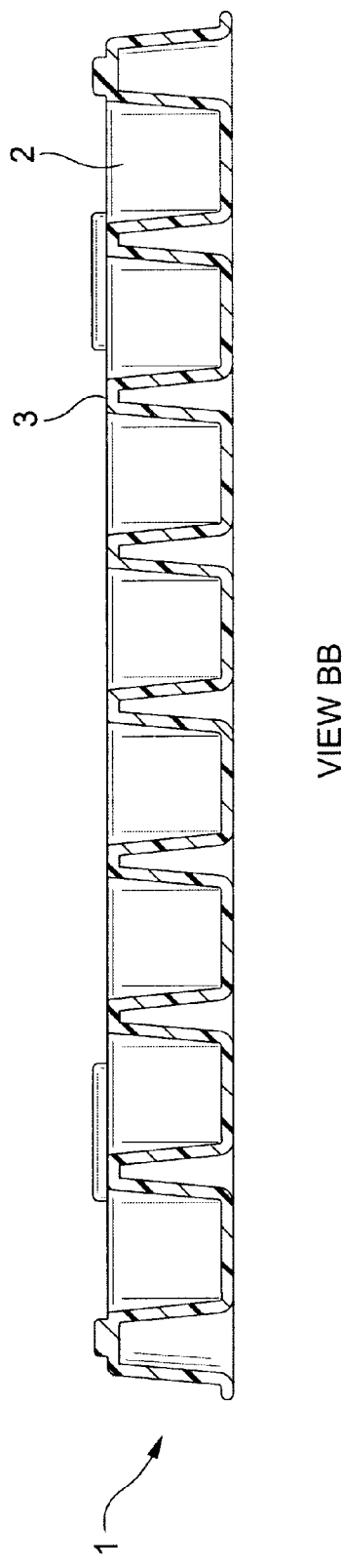
FIG. 2 is a view of the multi-channel dish taken along line B—B.
Figure 3:
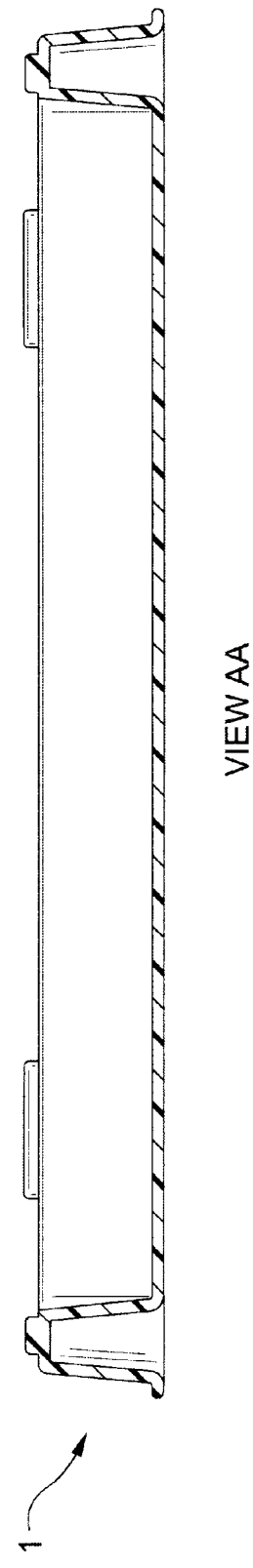
FIG. 3 is a view of the multi-channel dish taken along line A—A.

The present invention is a container 1 which is rectilinear in shape, with a square shape or a rectangular shape being most suitable. One suitable shape and size is a square 3.66 inches by 3.66 inches with a depth of 0.34 inches. However, the particular size and shape can be varied as needed. For example, if the container is to be used in an automated process, the size of the container would be selected so as to be compatible with the automated equipment.

A lid (not shown) is desirable for a preferred embodiment of the container. In this preferred embodiment, the lid would fit over the container in an interlocking manner in order to maintain the microbial growth medium at a proper moisture level. If left uncovered and exposed to air, the moisture in the growth media could dissipate, making it unsuitable for use. The lid can also maintain asepsis and maintain the chemical integrity of the growth medium. The lid may be designed to permit the exchange of a controlled atmosphere that is required for the growth of the particular microorganism.

The container and its lid are preferably made of a plastic material which can be thermoformed, or made by an other suitable plastic forming process. Materials which are clear to permit viewing of the media and any growing bacteria are preferred, as are materials which are capable of retaining moisture. Examples of suitable materials include polyvinylchloride, polystyrenes, polycarbonates, and polyethylene. Selection of the appropriate plastic material is not crucial as long as the material is capable of retaining moisture and withstanding incubation conditions. Polyvinyl chloride has been used to manufacture suitable containers.

The container is divided into two or more parallel channels or troughs 2 by plastic dividers 3 which can be formed simultaneously with the container or inserted in a nonmovable fashion after the formation of the dish portion. The depth of each channel or trough is determined based on the amount of growth medium needed to sustain bacterial growth, and would be well known to those of ordinary skill in the art. A depth of 0.34 inches has been used to make a container in accordance with the present invention. The dividers may be a single sheet of plastic or two pieces of plastic arranged side by side, as long as channels of equal width are created.

The depth of the channels can be varied along a gradient if desired so that the growth medium will create a wedge shape when filled into the device.

The number of channels is not crucial and should be selected to suit the particular needs of the assay to be run. For example if it is typical to do six serial dilutions of a sample, a six channel plate may be appropriate. Addition of another channel as a control may also be desired. Selection of the number of channels is not crucial, however it is considered likely that the number used will most usually be between four and eight.

While the channels can be created so as to run the entire length of the multi-channel dish, another configuration is possible. The channels may run nearly the full length of the dish, so that an open end area or reservoir is created at one end of the dish whereby all the channels connect equally at the open end. In such a case, the open end area spans the entire width of the container so as to act as a conduit for the purpose of receiving a gelling matrix to provide for equal distribution of the matrix and facilitate distribution of a microbial inoculum throughout all the channels. An open end area of 0.125 inches in width is suitable, although other sizes can be used depending on the nature of the tests to be conducted.

The channels or troughs so constructed are intended to be filled with a growth matrix or medium for microbes. The multi-channel dish can be manufactured and sold without containing any growth media. In such a case, the purchaser or end user of the multi-channel plate would fill the plate with the desired growth medium using accepted practices. Alternatively, the multi-channel plates can be filled with various growth media and sent to end-users ready-to-use.

Growth media which can be used in the multi-channel plate are any of those which are considered to be solid or semi-solid growth media. Suitable examples are well known to those of ordinary skill in the art and include media listed in, for example, The Manual of BBL Products and Laboratory Procedures, Sixth Edition (1988). More specifically, solid growth media which can be used in the multi-channel plate of the present invention include various agars, such as Mueller Hinton Agar, as well as those containing blood products, such as Chocolate Agar and Trypticase® Soy Agar with Sheep Blood. Those skilled in the art are aware of other media that could be used in this invention.

Any microorganism which can be enumerated or identified using solid growth media may be evaluated using the product and process of this invention, including but not limited to bacteria, yeast, fungi and protozoa. To exemplify, and not limit the scope of this invention, such suitable microorganisms include *Escherichia coli*.

It is apparent that the multi-channel plate can be filled with one type of microbial growth medium and this would be suitable when enumeration of one suspected microorganism in a given sample was sought. However, the present invention also contemplates instances where more than one growth medium can be included in a single multi-channel plate. For example, one might not only want to enumerate the bacteria strongly suspected of being in a given sample, one might also simultaneously wish to identify other microorganisms which might be in the sample. To accomplish this, some of the channels can contain a general growth medium while other channels contain one or more growth media that are selective and/or differential for the microorganism to be enumerated.

Yet another possibility is a situation where two different microorganisms are suspected of being in a sample. By the selection of appropriate growth media, they can be enumerated simultaneously.

As another possibility, some of the channels may contain a selective growth medium for the microorganism to be enumerated as well as a growth medium containing chromogens which permit the identification of various microorganisms from a mixed sample. Examples of chromogen containing growth media are well known in the art and examples may be found in the literature such as No. 94/08043, U.S. Pat. No. 5,210,022 and U.S. Pat. No. 5,464, 755.

Other substances such as antigens, toxins, enzymes, or nutrients which aid in identifying specific colony types can be added to the growth medium. Indeed, each channel can have a growth medium which varies from the adjacent channel by the addition of an ingredient which serves to distinguish and make qualitative or quantitative categorizations between mixed colonies.

Filling the multi-channel plate with the selected growth medium can be done by any accepted method, such as described in the Manual of BBL Products and Laboratory Procedures, 6th Edition (1988), which is incorporated by reference in its entirety herein.

To use the channel dish as a means of enumerating bacteria in a sample, one prepares the sample containing the microorganism in accordance with accepted and known procedures. For example, a biological fluid suspected of containing pathogenic bacteria will be either analyzed immediately or kept under refrigeration until it can be subjected to serial dilution. After the serial dilutions are made, for example six, ten-fold dilutions, a uniform quantity of each dilution, e.g., 10 uL is deposited at the head of each channel. A micropipet is suitable for this purpose, although the use of automated systems to deliver the sample to each channel is also envisioned by the present invention. The channels can be pre-labeled if desired. The multi-channel dish which has now been inoculated with bacterial samples is tilted to distribute the bacteria containing sample throughout the length of the container. The tilting can be done manually or by an automated process. The angle of tilt is not crucial as long as it is uniformly applied and permits the flow of sample down the growth media in each channel.

After a short time sufficient for the liquid sample to adsorb into the medium, the inoculated multi-channel plate is incubated.

If the results are to be determined visually, incubation on the order of 16–24 hours is usually necessary. Incubation conditions appropriate for the bacteria believed to be present and the growth medium selected are known to those skilled in the art.

Visual inspection of the plate after incubation will usually reveal channels where little or no measurable growth occurred as well as channels overgrown with bacteria. A channel containing a countable number of colonies is found and the colonies counted. The definition of a countable number will be determined by the method of visualization used. By multiplying the number of colonies counted by the dilution factor for that channel, the approximate number of bacteria in the sample can be calculated.

The present invention can also be used in an automated process and can be used so that high resolution image capture methods can be used to measure the number of bacteria. In such methods, the period for incubation can be greatly reduced, for example to 3 to 6 hours from 16–24 hours. Use of a high resolution camera at this stage would permit an accurate count of the bacteria the same day the sample was collected. This ability has important ramifications in the event of a public health problem such as contaminated water, but also in the individual assessment of a patient's condition. Moreover, the more rapid measurement of the amount of microorganisms or the identity of the microorganisms permits more throughput of samples, thus increasing efficiency and reducing costs. In addition, the accuracy of counting a greater number of colonies per plate is greatly enhanced. For example, visual enumeration limits accurate counting to 200–300 colonies. A high resolution image processor could accurately count thousands of microcolonies, reducing the number of dilutions needed to quantify highly concentrated samples.

Indeed, with the multi-channel plate and high-resolution image capture methods such as a digital camera and the use of software, one may be able to totally automate this highly labor intensive process. A digital camera useful for this purpose is a Kodak DC 210 Zoom, available from Kodak. Software appropriate for this use is Adobe PhotoDeluxe 2.0, available from general software retailers. Methods of concentrating the samples, such as filtration and centrifugation can be added to make a more completely automated process.

By selection of appropriate media, channel lengths and depths it may also be possible to use the multi-channel dish described herein to determine susceptibility of bacteria to various antibiotics as well as to determine Minimum Inhibitory Concentrations (MICs) and the like, by developing uniform antibiotic gradients within each channel. A paper disc of appropriate diameter containing the appropriate antibiotic can be tamped against the distal end of a channel immediately after inoculation of the gelled growth matrix. Diffusion of the antibiotic is restricted to said channel, growth inhibition distance is measured by a suitable caliper, the distance converted to an MIC value. The use of troughs having a wedge-shaped profile would effectively create a continuous gradient of antibiotic concentration and permit quantification of MIC as in the so-called gradient-plate method.

The following example is set forth to demonstrate the present invention but not to limit its scope.

EXAMPLE 1

A square polyvinyl container 3.66×3.66 inches is thermoformed of polyvinyl chloride. Eight parallel channels are created by spacers evenly dispersed in the container. The depth of each channel is uniform at 0.34 inches. A growth medium, Mueller Hinton Agar, is poured into the sterilized container and allowed to solidify. The filled multi-channel plate is then covered with a polyvinylchloride lid until use.

Four ten-fold serial dilutions of a fluid sample or specimen (urine, for example) suspected of containing $10^6$ CFU/mL, more or less, are made in accordance with accepted practices. Using a micropipet, 10 uL of each dilution are placed at the top end of each channel which has been appropriately labeled in advance. Once each channel has been inoculated, the plate is tipped at an angle of 45° for a time sufficient to permit each sample to run the length of the channel. The multi-channel plate is then returned to a flat position and the liquid allowed to adsorb into the media for 2 minutes. The plate is then subjected to incubation at 35° C., for example, for 24 hours. After 24 hours, the multi-channel plate is removed from the incubator. Those channels where microbial growth is capable of being counted accurately are enumerated. The number of colonies counted is then multiplied by the dilution factor indicated on the label at the end of the multi-channel plate to obtain the number of bacteria in the original sample.

The example set forth above is illustrative and is not meant to limit the scope of the present invention.

What we claim is:

1. A rectilinear plastic container having one or more dividers separating the interior space of the container into two or more channels wherein each channel contains a microbial growth medium, wherein the plastic is selected from the group consisting of polyvinyl chloride, polyethylene, polycarbonates and polystyrenes.

2. The container according to claim 1 wherein the plastic is polyvinylchloride.

3. The container according to claim 1 wherein different microbial growth media are contained in adjacent channels.

4. The container according to claim 1 wherein the microbial growth medium is a general growth medium or a single growth medium.

5. The container according to claim 1 wherein the microbial growth medium is a selective and/or differential growth medium.

6. The container according to claim 1 wherein the microbial growth medium contains one or more of a chromogen, an enzyme, an antigen, a nutrient or a toxin.

7. The container according to claim 1 wherein the depth of the container varies along its length.

8. The container according to claim 1 wherein the container has a lid.

9. The container according to claim 8 wherein the lid is plastic and the lid maintains the moisture level and atmospheric conditions of the microbial growth medium within the container.

10. The container according to claim 7 wherein the dividers do not run the full length of said container.

11. A process for enumerating microorganisms in a sample, said process comprising:
   a) serially diluting the sample by at least a first dilution wherein said dilution is selected from the group consisting of a two-fold dilution, five-fold dilution and ten-fold dilution;
   b) depositing a measured amount of undiluted sample or said at least first dilution containing sample on a microbial growth medium wherein said microbial growth medium is situated in a channel created by at least one divider in a rectilinear plastic container;
   c) making the undiluted sample or at least first dilution traverse the length of the container manually or by an automated process;
   d) optionally, allowing excess liquid from the sample or dilution to adsorb into the inoculated surface of the container for a short period of time;
   e) incubating the container for a set period of time to promote microbial growth; and
   f) enumerating the microorganisms in the sample after the set period of time has passed.

12. The process of claim 11 wherein after the set period of time has passed, the microbial growth medium in the channels are visually inspected for microbial growth.

13. The process of claim 11 wherein after the set period of time has passed, the microbial growth medium in the channels are inspected by a mechanical or physical means.

14. The process of claim 13 wherein the mechanical means includes a high-resolution image capture device.

15. The process of claim 12 wherein the number of microorganism colonies grown in one or more channels containing microbial growth medium are counted.

16. The process of claim 12 wherein the number of microorganism colonies grown in one or more channels containing microbial growth medium are counted.

17. The process of claim 11 wherein the microorganisms are capable of forming colonies including bacteria, yeast, fungi, or protozoa.

18. The process of claim 11 wherein the plastic of said plastic container is selected from the group consisting of polyvinylchloride, polyethylene, polycarbonates and polystyrenes.

19. The process of claim 11 wherein the microbial growth medium is a general growth medium or a selective and/or differential growth medium.

20. The process of claim 11 wherein the microbial growth medium contains one or more of a chromogen, an enzyme, an antigen, a nutrient or a toxin.

21. The process of claim 11 wherein said container has two or more channels wherein each channel contains a microbial growth medium.

22. The process of claim 21 wherein different microbial growth media are contained in adjacent channels.

23. The process of claim 11 wherein the container has a lid.

24. The process of claim 23 wherein the lid is plastic and the lid maintains the moisture level and atmospheric conditions of the microbial growth medium within the container.

25. The process of claim 11 wherein the depth of the container varies along its length, and further wherein the dividers do not run the full length of said container.

26. The process of claim 11 wherein the set period of time for incubation of the container is from about 16 hours to about 24 hours.

27. The process of claim 11 wherein the set period of time for incubation of the container is from about 3 hours to about 16 hours.

28. A process for enumerating microorganisms in a sample, said process comprising:
   a) serially diluting the sample by at least a first dilution wherein said dilution is selected from the group consisting of a two-fold dilution, five-fold dilution and ten-fold dilution;
   b) depositing a measured amount of undiluted sample or said at least first dilution containing sample on a microbial growth medium wherein said microbial growth medium is situated in a channel created by at least one divider in a rectilinear plastic container;
   c) making the undiluted sample or at least first dilution traverse the length of the container manually or by an automated process;
   d) optionally, allowing excess liquid from the sample or dilution to adsorb into the inoculated surface of the container for a short period of time;
   e) incubating the container for varying time intervals to promote microbial growth; and
   f) enumerating the microorganisms in the sample at the varying time intervals.

* * * * *